US008560969B2

United States Patent
Abasov et al.

(10) Patent No.: US 8,560,969 B2
(45) Date of Patent: Oct. 15, 2013

(54) SYSTEMS AND METHODS FOR IMAGING OPERATIONS DATA IN A THREE-DIMENSIONAL IMAGE

(75) Inventors: Shahin Abasov, Houston, TX (US); Ron Mossbarger, Houston, TX (US)

(73) Assignee: Landmark Graphics Corporation, Houston, TX (US)

( * ) Notice: Subject to any disclaimer, the term of this patent is extended or adjusted under 35 U.S.C. 154(b) by 1231 days.

(21) Appl. No.: 12/215,336

(22) Filed: Jun. 26, 2008

(65) Prior Publication Data

US 2009/0327970 A1 Dec. 31, 2009

(51) Int. Cl.
*G06F 3/048* (2013.01)

(52) U.S. Cl.
USPC ........... 715/849; 715/848; 345/419; 345/440; 703/10; 702/12

(58) Field of Classification Search
USPC ......................................................... 715/849
See application file for complete search history.

(56) References Cited

U.S. PATENT DOCUMENTS

| | | | | |
|---|---|---|---|---|
| 5,608,849 A * | 3/1997 | King, Jr. | | 345/419 |
| 6,012,018 A * | 1/2000 | Hornbuckle | | 702/16 |
| 6,519,531 B1 * | 2/2003 | Batycky et al. | | 702/12 |
| 7,098,908 B2 * | 8/2006 | Acosta et al. | | 345/419 |
| 7,155,042 B1 * | 12/2006 | Cowan et al. | | 382/128 |
| 7,289,942 B2 * | 10/2007 | Yang et al. | | 703/10 |
| 7,369,973 B2 * | 5/2008 | Kennon et al. | | 703/2 |
| 7,584,086 B2 * | 9/2009 | Frankel | | 703/10 |
| 7,634,395 B2 * | 12/2009 | Flandrin et al. | | 703/10 |
| 7,660,711 B2 * | 2/2010 | Pita et al. | | 703/10 |
| 7,680,640 B2 * | 3/2010 | Camilleri | | 703/10 |
| 7,765,091 B2 * | 7/2010 | Lee et al. | | 703/10 |
| 7,792,565 B2 * | 9/2010 | Vining | | 600/407 |
| 7,836,674 B2 * | 11/2010 | Meixner et al. | | 57/265 |
| 7,844,320 B2 * | 11/2010 | Shahidi | | 600/424 |
| 7,853,310 B2 * | 12/2010 | Vining et al. | | 600/425 |
| 7,882,438 B2 * | 2/2011 | Markham et al. | | 715/736 |
| 7,961,188 B2 * | 6/2011 | Tolle et al. | | 345/440 |
| 2002/0035443 A1 * | 3/2002 | Matteucci et al. | | 702/155 |
| 2004/0174357 A1 * | 9/2004 | Cheung et al. | | 345/419 |
| 2005/0024360 A1 * | 2/2005 | Abe et al. | | 345/419 |
| 2006/0184329 A1 * | 8/2006 | Rowan et al. | | 702/50 |
| 2006/0189829 A1 * | 8/2006 | Burlone et al. | | 568/410 |
| 2006/0246844 A1 * | 11/2006 | Kroboth et al. | | 455/67.11 |
| 2006/0282243 A1 * | 12/2006 | Childs et al. | | 703/10 |
| 2007/0016389 A1 * | 1/2007 | Ozgen | | 703/10 |
| 2007/0027666 A1 * | 2/2007 | Frankel | | 703/10 |
| 2007/0071413 A1 * | 3/2007 | Takahashi et al. | | 386/96 |
| 2007/0255545 A1 * | 11/2007 | Pita et al. | | 703/10 |
| 2008/0165185 A1 * | 7/2008 | Smith et al. | | 345/419 |
| 2008/0195930 A1 * | 8/2008 | Tolle | | 715/227 |

(Continued)

*Primary Examiner* — William Bashore
*Assistant Examiner* — Reza Nabi
(74) *Attorney, Agent, or Firm* — Crain, Caton & James; Bradley A. Misley (57) ABSTRACT

Systems and methods for imaging operations data as a three-dimensional image, which include rendering a three-dimensional image of an object having at least one attribute, a marker in the object, and one or more operations values relative to one or more respective positions on the marker in the object. A data structure comprising a data field, the data field comprising a three-dimensional image of an object having at least attribute, a marker and one or more operations values relative to one or more respective positions on the marker in the object at a selected time.

21 Claims, 4 Drawing Sheets
(2 of 4 Drawing Sheet(s) Filed in Color)

(56) References Cited

U.S. PATENT DOCUMENTS

| | | |
|---|---|---|
| 2008/0208539 A1* | 8/2008 | Lee et al. .......................... 703/1 |
| 2008/0230728 A1* | 9/2008 | Meixner et al. .......... 250/559.27 |
| 2009/0043549 A1* | 2/2009 | Peng ................................. 703/6 |
| 2009/0114522 A1* | 5/2009 | Burlone et al. ................. 203/38 |
| 2009/0150097 A1* | 6/2009 | Camilleri ........................ 702/45 |
| 2009/0273599 A1* | 11/2009 | Abasov et al. ................ 345/419 |
| 2011/0015909 A1* | 1/2011 | Zhao ................................ 703/2 |
| 2011/0202442 A1* | 8/2011 | Rabstejnek ..................... 705/34 |

* cited by examiner

SYSTEMS AND METHODS FOR IMAGING OPERATIONS DATA IN A THREE-DIMENSIONAL IMAGE

CROSS REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention generally relates to systems and methods for selectively imaging operations data in a three-dimensional image comprising multiple three-dimensional objects. More particularly, the present invention relates to imaging operations values in a three-dimensional image relative to a marker and an object.

BACKGROUND OF THE INVENTION

In some fields, it is useful to model objects in three dimensions. Modeling such objects proves useful in a variety of applications, particularly when the object includes operations data. For example, modeling the progress of treatments in the human body is useful for medical training exercises, diagnoses, performing remote surgery or for other medical applications. Similarly, modeling the production of wells in a reservoir is useful for production operations and evaluating the results of reservoir stimulation. The foregoing objects are exemplary only, and other fields may likewise find utility in modeling various objects.

In the field of life sciences, data may be compiled for various treatments, such as chemotherapy, at various points in the body. This may be particularly helpful for modeling and/or monitoring the administration of such treatment directly to various points on a tumor based upon the reaction of the tumor.

In the field of earth sciences, operations data is compiled for a production well at various perforated intervals along the length (depth) of the well to aid in increasing production from a reservoir. In such systems, the operations data are recorded relative to various perforated intervals along the length of the well and various times. The operations data therefore, typically include one or more operations values for a selected time and the (depth) position of each operations value relative to the well.

Operations data is often presented in two-dimensional formats, such as a pie chart a bar chart, or a bubble chart. Two-dimensional data formats, however, fail to convey other essential data such as, for example, the relationships between different operations data for a well at different times relative to the reservoir. Two-dimensional formats are particularly inefficient when attempting to gain a global perspective of the reservoir or another object. When the number of production wells increases, the two-dimensional data format becomes even more awkward to use.

Thus, there is a need for imaging operations data in a three-dimensional image which includes an image of one or more operations values relative to each other, a marker and a related object.

SUMMARY OF THE INVENTION

The present invention therefore, meets the above needs and overcomes one or more deficiencies in the prior art by providing systems and methods for imaging operations data in a three-dimensional image.

SUMMARY OF THE INVENTION

In one embodiment, the present invention includes a method for imaging operations data as a three-dimensional image, which comprises i) rendering an object having at least one attribute; ii) rendering a marker through an opening in the object, the marker having operations data relative to at least one position on the marker in the object and at least one time; iii) processing the operations data to produce one or more operations values at a selected time; iv) rendering a three-dimensional image of the marker, each operations value relative to its respective position on the marker in the object and the object; and v) moving the opening to obtain a different perspective of the marker and each operations value relative to the object as the opening is moved.

In another embodiment, the present invention includes a computer-readable medium having computer executable instructions for imaging operations data as a three-dimensional image. The instructions are executable to implement i) rendering an object having at least one attribute; ii) rendering a marker through an opening in the object, the marker having operations data relative to at least one position on the marker in the object and at least one time; iii) processing the operations data to produce one or more operations values at a selected time; iv) rendering a three-dimensional image of the marker, each operations value relative to its respective position on the marker in the object and the object; and v) moving the opening to obtain a different perspective of the marker and each operations value relative to the object as the opening is moved.

In yet another embodiment, the present invention includes a computer-readable medium having a data structure stored thereon, the data structure comprising a data field, the data field comprising a three-dimensional image of an object having at least one attribute, a marker rendered through an opening in the object and one or more operations values relative to one or more respective positions on the marker in the object at a selected time.

Additional aspects, advantages and embodiments of the invention will become apparent to those skilled in the art from the following description of the various embodiments and related drawings.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

The present invention is described below with references to the accompanying drawings in which like elements are referenced with like numerals, and in which.

DETAILED DESCRIPTION OF THE PREFERRED EMBODIMENTS

The subject matter of the present invention is described with specificity; however, the description itself is not intended to limit the scope of the invention. The subject matter thus, might also be embodied in other ways, to include different steps or combinations of steps similar to the ones described herein, in conjunction with other present or future technologies. Moreover, although the term "step" may be used herein to describe different elements of methods employed, the term should not be interpreted as implying any particular order among or between various steps herein disclosed unless otherwise expressly limited by the description to a particular order.

Method Description

Figure 1:
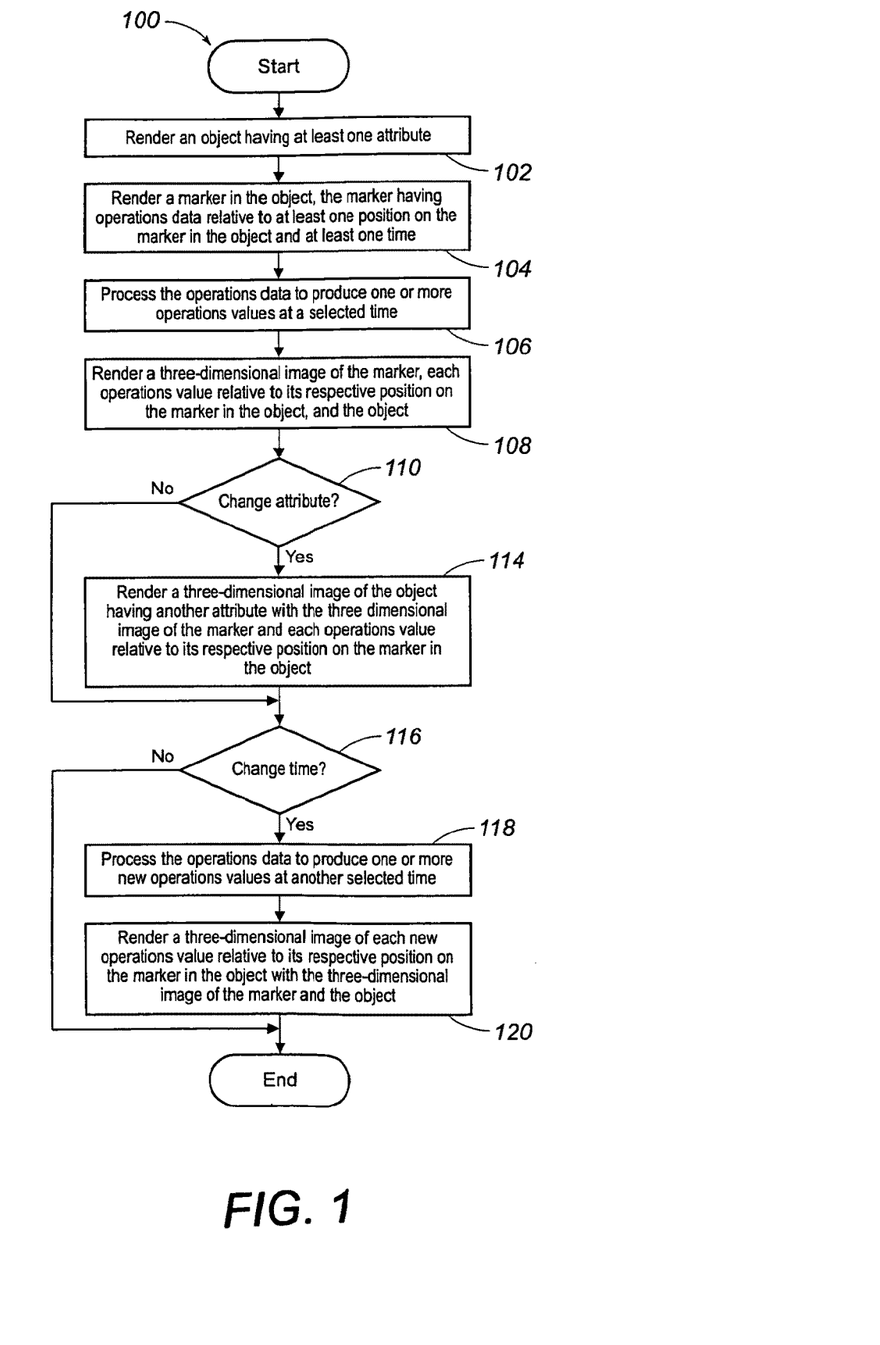
FIG. 1 is a flow diagram illustrating one embodiment of a method for implementing the present invention.

Referring now to FIG. 1, a flow diagram illustrates one embodiment of a method 100 for implementing the present invention.

In step 102, an object having at least one attribute is rendered using conventional graphical rendering techniques, which are well known in the art.

In step 104, a marker is rendered in the object using conventional graphical rendering techniques, which are well known in the art. The marker may be rendered based upon a predetermined position for the marker or a selected position for the marker. The marker includes operations data relative to at least one position on the marker in the object and at least one time.

In step 106, the operations data is processed to produce one or more operations values at a selected time. The operations values may represent any data of importance such as, for example, a production rate, a fluid factor, a velocity or a pressure.

In step 108, a three-dimensional image of the marker, each operations value relative to its respective position on the marker in the object, and the objected are rendered using conventional graphical rendering techniques, which are well known in the art.

In step 110, the method 100 determines whether there is a request to change the attribute. If there is a request to change the attribute, then the method 100 proceeds to step 114. If there is no request to change the attribute, then the method 100 proceeds to step 116.

In step 114, a three-dimensional image of the object having another attribute is rendered with the three-dimensional image of the marker and each operations value relative to its respective position on the marker in the object using conventional graphical rendering techniques, which are well known in the art.

In step 116, method 100 determines whether there is a request to change the time. If there is a request to change the time, then the method 100 proceeds to step 118. If there is no request to change the time, then the method 100 proceeds to the end.

In step 118, the operations data is processed to produce one or more new operations values at another selected time. Again, the operations values may represent any data of importance such as, for example, a production rate, a fluid factor, a velocity or a pressure.

In step 120, a three-dimensional image of each new operations value relative to its respective position on the marker in the object is rendered with the three-dimensional image of the marker and the object using conventional graphical rendering techniques, which are well known in the art.

System Description

The present invention may be implemented through a computer-executable program of instructions, such as program modules, generally referred to as software, being executed by a computer. Generally, program modules include routines, programs, objects, components, data structures, etc., that perform particular tasks or implement particular abstract data types. The software forms an interface to allow a computer to react according to a source of input. AssetView®, which is a commercial software application marketed by Landmark Graphics Corporation, may be used as an interface application to implement the present invention. AssetView® provides the tools by which the user may visually restrict the data displayed to the relationships of interest and review the data presented in an uncluttered manner, particularly when multiple relationships are to be concurrently communicated. The software may also cooperate with other code segments to initiate a variety of tasks in response to data received in conjunction with the source of the received data. The software may be stored onto any variety of memory media such as CD-ROM, magnetic disk, bubble memory and semiconductor memory (e.g., various types of RAM or ROM). Furthermore, the software and its results may be transmitted over a variety of carrier media such as optical fiber, metallic wire, free space and/or through any of a variety of networks such as the internet.

Additionally, the software may include a data structure stored thereon. The data structure may comprise one or more data fields, at least one data field comprising a three-dimensional image of an object having at least one attribute, a marker and one or more operations values relative to one or more respective positions on the marker in the object at a selected time step. Each operations value may be represented by one of a cylinder or a bar. Preferably, each operations value may be represented by at least one of a color and a diameter for the cylinder or a color and a length for the bar. Optionally, each operations value may be represented by a numeric value on the cylinder or the bar. The object may be translucent for displaying the marker and each operations value. Optionally, the object may be opaque for displaying the marker and the operations value through an opening in the object. The at least one attribute represents one of amplitude, frequency, phase, power, semblance, coherency, dip, azimuth, gradient, fluid factor, acoustic impendence, velocity, pressure, porosity, permeability, stratigraphy and lithography. The object may comprise a three-dimensional reservoir grid having a plurality of grid cells, wherein each grid cell represents an attribute value. Each operations value may represent one of a production rate, a fluid factor, a velocity and a pressure. The data structure may further comprise another data field, wherein the another data field includes a three-dimensional image of the object having another attribute, and the three-dimensional image of the marker and each operations value relative to each respective position on the marker in the object. In addition, the data structure may comprise another data field, wherein the another data field includes a three-dimensional image of one or more new operations values relative to one or more respective positions on the marker in the object at another selected time step, and the three-dimensional image of the marker and the object.

Moreover, those skilled in the art will appreciate that the invention may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present invention, including local workstations and visualization stations. The invention may be practiced in distributed-computing environments where tasks are performed by remote-processing devices that are linked through a communications network. In a distributed-computing environment, program modules may be located in both local and remote computer-storage media including memory storage devices. The computer-executable instructions form an interface to allow a computer to react according to a source of input. The instructions cooperate with other code segments to initiate a variety of tasks in response to data received in conjunction with the source of the received data. The present invention may therefore, be implemented in connection with various hardware, software or a combination thereof, in a computer system or other processing system.

Figure 2:
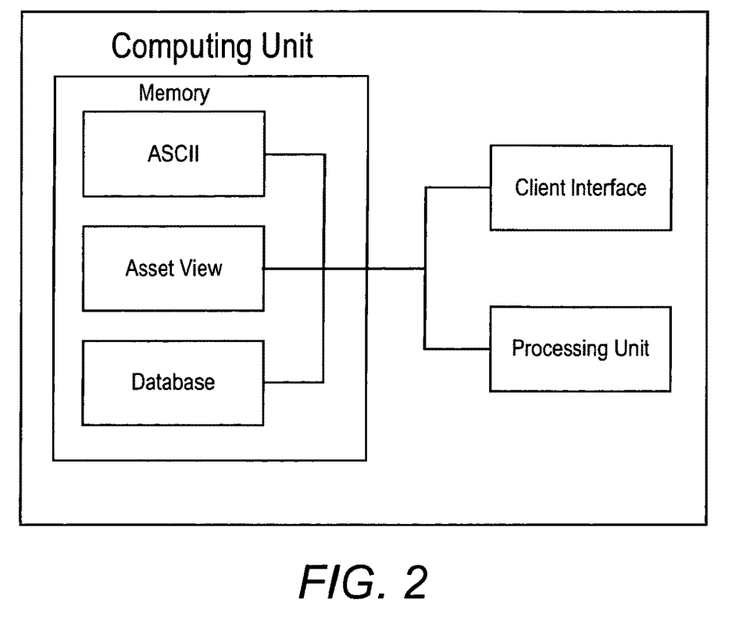
FIG. 2 is a block diagram illustrating one embodiment of a computer system for implementing the present invention.

Referring now to FIG. 2, a block diagram of a system for implementing the present invention on a computer is illustrated. The system includes a computing unit, sometimes referred to a computing system, which contains memory, application programs, a data base, ASCII files, a client interface, and a processing unit. The computing unit is only one example of a suitable computing environment and is not intended to suggest any limitation as to the scope of use or functionality of the invention.

The memory primarily stores the application programs, which may also be described as a program module containing computer-executable instructions, executed by the computing unit for implementing the present invention described herein and illustrated in FIG. 1. The memory also includes AssetView®, which can be used to display data and data results. The memory database may be used to supply data and store data results. ASCII files may also be used to supply data and store data results.

Although the computing unit is illustrated as having a generalized memory, the computing unit typically includes a variety of computer readable media. By way of example, and not limitation, computer readable media may comprise computer storage media and communication media. The computing system memory may include computer storage media in the form of volatile and/or nonvolatile memory such as a read only memory (ROM) and random access memory (RAM). A basic input/output system (BIOS), containing the basic routines that help to transfer information between elements within the computing unit, such as during start-up, is typically stored in ROM. The RAM typically contains data and/or program modules that are immediately accessible to and/or presently being operated on by the processing unit. By way of example, and not limitation, the computing unit includes an operating system, application programs, other program modules, and program data.

The components shown in the memory may also be included in other removable/nonremovable, volatile/nonvolatile computer storage media. For example only, a hard disk drive may read from or write to nonremovable, nonvolatile magnetic media, a magnetic disk drive may read from or write to a removable, non-volatile magnetic disk, and an optical disk drive may read from or write to a removable, nonvolatile optical disk such as a CD ROM or other optical media. Other removable/non-removable, volatile/non-volatile computer storage media that can be used in the exemplary operating environment may include, but are not limited to, magnetic tape cassettes, flash memory cards, digital versatile disks, digital video tape, solid state RAM, solid state ROM, and the like. The drives and their associated computer storage media discussed above provide storage of computer readable instructions, data structures, program modules and other data for the computing unit.

A client may enter commands and information into the computing unit through the client interface, which may be input devices such as a keyboard and pointing device, commonly referred to as a mouse, trackball or touch pad. Input devices may include a microphone, joystick, satellite dish, scanner, or the like.

These and other input devices are often connected to the processing unit through the client interface that is coupled to a system bus, but may be connected by other interface and bus structures, such as a parallel port or a universal serial bus (USB). A monitor or other type of display device may be connected to the system bus via an interface, such as a video interface. In addition to the monitor, computers may also include other peripheral output devices such as speakers and printer, which may be connected through an output peripheral interface.

Although many other internal components of the computing unit are not shown, those of ordinary skill in the art will appreciate that such components and the interconnection are well known.

EXAMPLES

Figure 3:
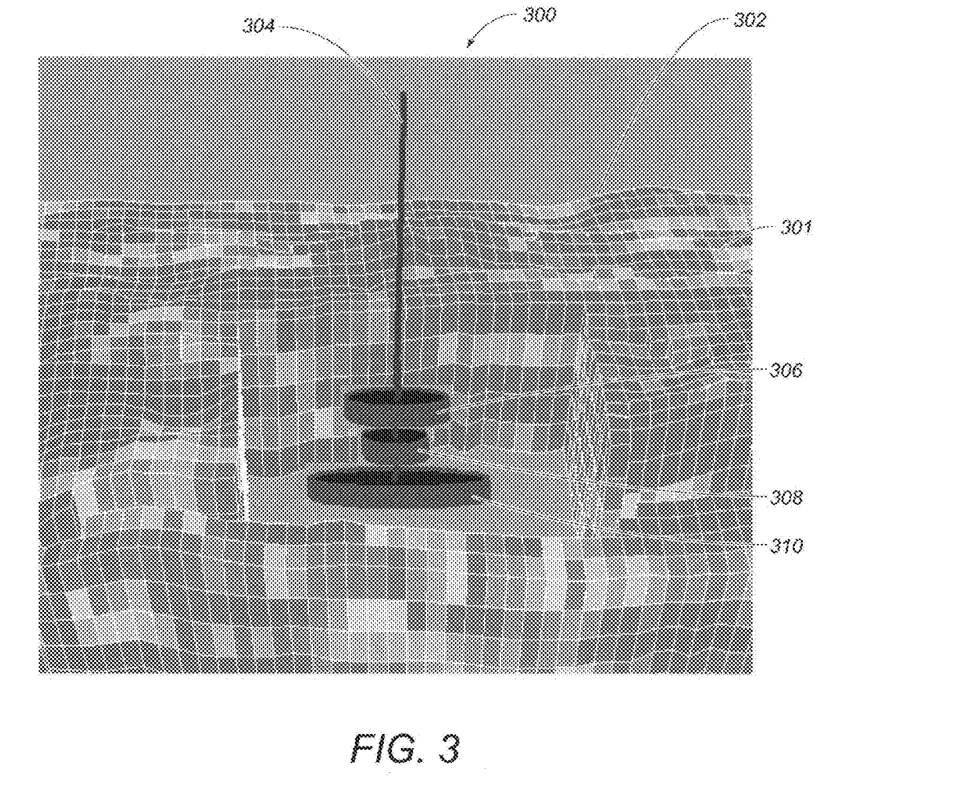
FIG. 3 is an exemplary color display illustrating one implementation of the present invention for rendering a well and three operations values within a three-dimensional reservoir grid.

Referring now to FIGS. 1 and 3, an exemplary display 300 illustrates one implementation of the present invention for rendering a production well (marker) and three operations values within a three-dimensional reservoir grid (object). The display 300 includes an image of the reservoir grid 302, a plurality of operations values (306, 308, 310) and a production well 304, which are rendered according to step 108 of method 100. The operations values (306, 308, 310) and the production well 304 are therefore, rendered in relation to the reservoir grid 302 and each other. As illustrated in FIG. 3, the various operations values (306, 308, 310) and production well 304 are rendered in the reservoir grid 302.

The reservoir grid 302 also includes at least one attribute, which is illustrated in FIG. 3 by various colors. The attribute in this example represents an amplitude associated with each cell 301 of the reservoir grid 302. Each cell 301 represents an attribute value that is associated with a particular color. Additional attributes, such as frequency, phase, power, semblance, coherency, dip, azimuth, gradient, fluid factor, acoustic impedance, velocity, pressure, porosity, permeability, stratigraphy and lithology may be included in the reservoir grid 302 and distinguished by a different color for each attribute. One attribute may also be substituted for another attribute as reflected by step 110 in method 100. In this manner, a three-dimensional image of the reservoir grid 302 may be rendered according to step 114 of method 100 with another attribute and the three-dimensional image of the production well 304 and each operations value (306, 308, 310) relative to its respective position on the production well 304 in the reservoir grid 302. The attribute values represented on the reservoir grid 302 therefore, may be used as an intuitive visual aid to distinguish areas of higher oil/gas concentration in part of the reservoir represented by the reservoir grid 302.

Each production well 304 includes operations data relative to at least one position on the production well 304 in the reservoir grid 302 and at least one time. In other words, the production well 304 is associated with operations data relative to some position on the production well 304 in the reservoir grid 302 at a selected time. The operations data associated with the production well 304 corresponds with the operations values (306, 308, 310), which are determined by processing the operations data in step 106 of the method 100 at the selected time. Another time may be selected as reflected by step 116 in method 100. In this event, the operations data associated with the production well 304 are processed according to step 118 of method 100 to produce one or more new operations values at another selected time. A three-dimensional image of each new operations value relative to its respective position on the production well 304 in the reservoir grid 302 may be rendered according to step 120 of method 100 with the three-dimensional image of the production well 304 and the reservoir grid 302.

Each operations value (306, 308, 310) may convey various operations data of interest to a user, such as a production rate, a fluid factor, a velocity and a pressure. Each operations value may be determined based on well known existing methods and represented by one of a cylinder or a bar. Optionally, each operations value may be represented by at least one of a color and a diameter for the cylinder or a color and a length for the bar. In addition, each operations value may be represented as a numeric value on the cylinder or the bar and selectively displayed as an interface device passes over the operations value.

Each operations value (306, 308, 310) may be associated with a perforated well interval in the reservoir grid 302. The reservoir grid 302 therefore, may include an attribute, meaning it is opaque, as illustrated in FIG. 3 for displaying the production well 304 and each operations value (306, 308, 310) through an opening in the reservoir grid 302. In this manner, each operations value (306, 308, 310) may be rendered in the display 300 relative to its respective position on the production well 304 and the reservoir grid 302 for determining optimal production rates and/or intervals along the production well 304 relative to an attribute value displayed on the reservoir grid 302. The opening in the reservoir grid 302 may therefore, be moved to gain a different perspective of the production well 304 and each operations value (306, 308, 310) relative to the reservoir grid 302. While the coordinates for a production well will not change, the opening in the reservoir grid may be interactively moved and/or resized to gain a different perspective of the attribute values relative to the operations values. Optionally, the reservoir grid 302 may be translucent for displaying the production well 304 and each operations value (306, 308, 310).

Based on the operations data, including the operations values and the attribute values, the production well 304 may be controlled alone, or in combination with other production wells, to adjust a production rate for the reservoir represented by the reservoir grid 302. Therefore, additional production wells and/or operations values may be included in the display 300. Because the operations data is represented in a three-dimensional image on a single display, the relationships between each production well, each operations value and the reservoir grid, are easier to determine and compare than in conventional two-dimensional formats, particularly where multiple relationships need to be concurrently communicated.

Figure 4:
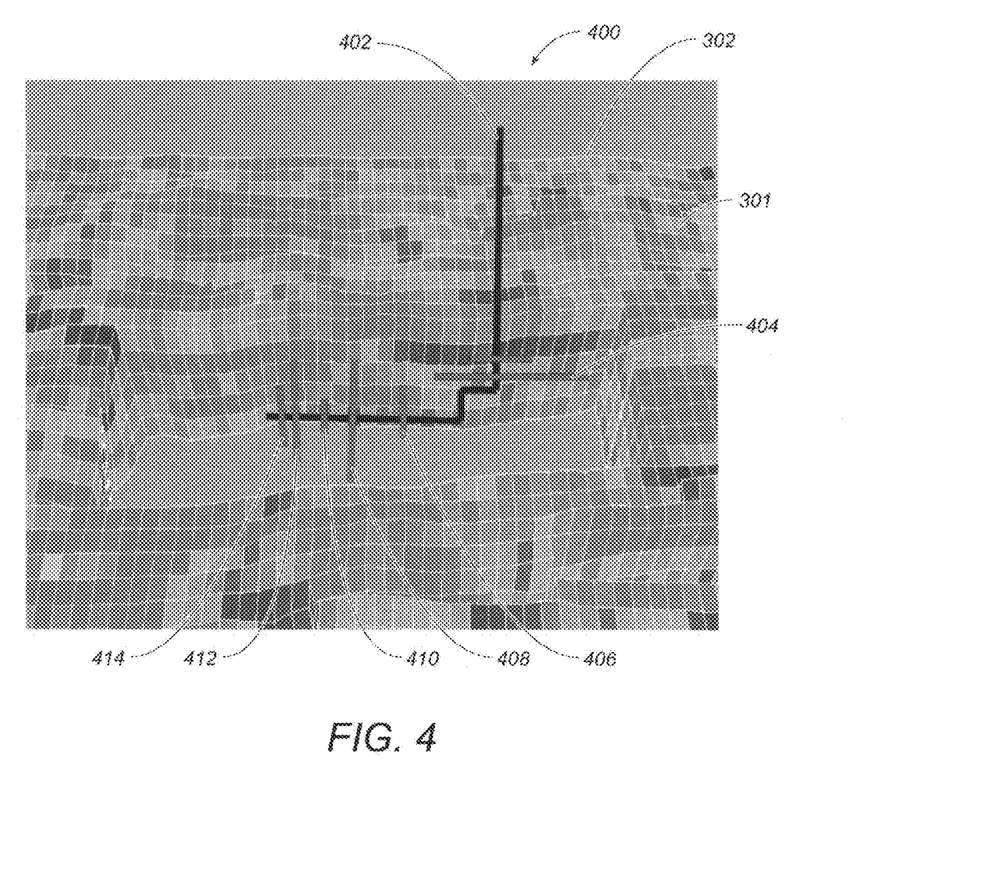
FIG. 4 is an exemplary color display illustrating one implementation of the present invention for rendering a deviated well and seven operations values within a three-dimensional reservoir grid.

Referring now to FIG. 4, an exemplary display 400 illustrates one implementation of the present invention for rendering a deviated production well (marker) and seven operations values within a three-dimensional reservoir grid (object). The display 400 includes an image of the reservoir grid 302, also illustrated in FIG. 3, a plurality of operations values (404, 406, 408, 410, 412, 414) and a deviated production well 402, which are rendered in substantially the same manner as the display 300. Each operations value (404, 406, 408, 410, 412, 414), however, is illustrated in a different manner than the operations values (306, 308, 310) illustrated in FIG. 3. In FIG. 4, for example, the operations values (404, 406, 408, 410, 412, 416) are illustrated as a red bar compared to the blue cylinders representing each operations value (306, 308, 310) in FIG. 3. In FIG. 3, the diameter of each operations value (306, 308, 310) is used to distinguish different values. Similarly, in FIG. 4, the length of each bar representing the operations values (404, 406, 408, 410, 412, 414) may be used to distinguish different values. In addition, each operations value may be distinguished from another operations value by a different color or numeric value displayed on the cylinder or the bar or selectively displayed as an interface device passes over the cylinder or the bar. As illustrated in FIGS. 3 and 4, each operations value is displayed perpendicular to the production well, however, need not be.

Additional applications in the same field may include, for example, a three-dimensional image of a drill string (marker) rendered in a three-dimensional image of an earth formation (object) having at least one attribute and one or more operations values rendered on the drill string in the earth formation. The operations values may represent, for example, formation data collected by sensors on the drill string.

Because the systems and methods described herein may be used to analyze operations data, they may be particularly useful in other fields, such as medicine, on human and/or animal bodies, and the like.

While the present invention has been described in connection with presently preferred embodiments, it will be understood by those skilled in the art that it is not intended to limit the invention to those embodiments. It is therefore, contemplated that various alternative embodiments and modifications may be made to the disclosed embodiments without departing from the spirit and scope of the invention defined by the appended claims and equivalents thereof.

The invention claimed is:

1. A method for imaging operations data as a three-dimensional image, which comprises:
    rendering an object having at least one attribute, wherein the object is either translucent or opaque;
    rendering a marker through an opening in the object for displaying the marker and each operation value through the opening in the object when the object is opaque, the marker having operations data relative to at least one position on the marker in the object and at least one time;
    processing the operations data to produce one or more operations values at a selected time;
    rendering a three-dimensional image of the marker, each operations value relative to its respective position on the marker in the object and the object; and
    moving the opening to obtain a different perspective of the marker and each operations value relative to the object as the opening is moved.

2. The method of claim 1, wherein each operations value is represented by one of a cylinder or a bar.

3. The method of claim 2, wherein each operations value is represented by at least one of a color and a diameter for the cylinder or a color and a length for the bar.

4. The method of claim 2, wherein each operations value is represented as a numeric value on the cylinder or the bar.

5. The method of claim 1, wherein the at least one attribute represents one of amplitude, frequency, phase, power, semblance, coherency, dip, azimuth, gradient, fluid factor, acoustic impendence, velocity, pressure, porosity, permeability, stratigraphy and lithography.

6. The method of claim 1, wherein the object is a three-dimensional reservoir grid having a plurality of grid cells.

7. The method of claim 6, wherein each grid cell represents an attribute value.

8. The method of claim 1, wherein each operations value represents one of a production rate, a fluid factor, a velocity, and a pressure.

9. The method of claim 1, further comprising:
rendering a three-dimensional image of the object having another attribute with the three-dimensional image of the marker and each operations value relative to its respective position on the marker in the object.

10. The method of claim 1, further comprising:
processing the operations data to produce one or more new operations values at another selected time; and
rendering a three-dimensional image of each new operations value relative to its respective position on the marker in the object with the three-dimensional image of the marker and the object.

11. The method of claim 1, further comprising:
displaying the three-dimensional image of the marker, each operations value relative to its respective position on the marker in the object and the object.

12. A non-transitory computer-readable medium having computer executable instructions for imaging operations data as a three-dimensional image, the instructions being executable to implement:
rendering an object having at least one attribute, wherein the object is either translucent or opaque;
rendering a marker through an opening in the object for displaying the marker and each operation value through the opening in the object when the object is opaque, the marker having operations data relative to at least one position on the marker in the object and at least one time;
processing the operations data to produce one or more operations values at a selected time;
rendering a three-dimensional image of the marker, each operations value relative to its respective position on the marker in the object and the object; and
moving the opening to obtain a different perspective of the marker and each operations value relative to the object as the opening is moved.

13. The non-transitory computer-readable medium of claim 12, wherein each operations value is represented by one of a cylinder or a bar.

14. The non-transitory computer-readable medium of claim 13, wherein each operations value is represented by at least one of a color and a diameter for the cylinder or a color and a length for the bar.

15. The non-transitory computer-readable medium of claim 13, wherein each operations value is represented as a numeric value on the cylinder or the bar.

16. The non-transitory computer-readable medium of claim 12, wherein the at least one attribute represents one of amplitude, frequency, phase, power, semblance, coherency, dip, azimuth, gradient, fluid factor, acoustic impendence, velocity, pressure, porosity, permeability, stratigraphy and lithography.

17. The non-transitory computer-readable medium of claim 12, wherein the object is a three-dimensional reservoir grid having a plurality of grid cells.

18. The non-transitory computer-readable medium of claim 17, wherein each grid cell represents an attribute value.

19. The non-transitory computer-readable medium of claim 12, wherein each operations value represents one of a production rate, a fluid factor, a velocity, and a pressure.

20. The non-transitory computer-readable medium of claim 12, further comprising:
rendering a three-dimensional image of the object having another attribute with the three-dimensional image of the marker and each operations value relative to each respective position on the marker in the object.

21. The non-transitory computer-readable medium of claim 12, further comprising:
processing the operations data to produce one or more new operations values at another selected time; and
rendering a three-dimensional image of each new operations value relative to each respective position on the marker in the object with the three-dimensional image of the marker and the object.

* * * * *